(12) United States Patent
Graham

(10) Patent No.: US 9,020,232 B2
(45) Date of Patent: Apr. 28, 2015

(54) PER VESSEL, VESSEL TREE MODELLING WITH SHARED CONTOURS

(75) Inventor: Alan Graham, Edinburgh (GB)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 68 days.

(21) Appl. No.: 13/556,705

(22) Filed: Jul. 24, 2012

(65) Prior Publication Data

US 2014/0029816 A1 Jan. 30, 2014

(51) Int. Cl.
*G06K 9/00* (2006.01)
*G06T 7/00* (2006.01)
*A61B 6/00* (2006.01)
*A61B 5/055* (2006.01)
*A61B 6/03* (2006.01)

(52) U.S. Cl.
CPC .............. *G06T 7/0012* (2013.01); *A61B 6/466* (2013.01); *A61B 6/504* (2013.01); *A61B 5/055* (2013.01); *A61B 6/032* (2013.01); *A61B 6/037* (2013.01)

(58) Field of Classification Search
CPC ........... G06T 2207/30172; G06T 2207/30101; G06T 17/00; G06T 19/00; A61B 5/489
USPC .................................................. 382/131, 132
See application file for complete search history.

(56) References Cited

U.S. PATENT DOCUMENTS

| | | | |
|---|---|---|---|
| 2002/0118869 A1 | 8/2002 | Knoplioch et al. | |
| 2004/0066958 A1* | 4/2004 | Chen et al. | 382/128 |
| 2004/0249270 A1 | 12/2004 | Kondo et al. | |
| 2008/0094389 A1* | 4/2008 | Rouet et al. | 345/419 |
| 2010/0021025 A1* | 1/2010 | Hof et al. | 382/128 |
| 2010/0092053 A1 | 4/2010 | Manabe et al. | |

FOREIGN PATENT DOCUMENTS

CN 1954340 A 4/2007

OTHER PUBLICATIONS

Office Action mailed Jan. 20, 2015, in Chinese Patent Application No. 201310312557.4.

* cited by examiner

*Primary Examiner* — Amir Alavi
*Assistant Examiner* — Kenny Cese
(74) *Attorney, Agent, or Firm* — Oblon, McClelland, Maier & Neustadt, L.L.P.

(57) ABSTRACT

A system and method that determines a contour of a model vessel representing a branching structure, wherein the structure contains a branch point at which an upper segment of the structure splits into a first lower segment and a second lower segment, and determines a path of a first model vessel representative of at least part of the upper segment and at least part of the first lower segment, determines a path of a second model vessel, representative of at least part of the upper segment and at least part of the second lower segment, determines the position of a contour branch point; and ensures that for at least one position above the contour branch point a contour of the first model vessel is substantially the same as a contour of the second model vessel.

21 Claims, 7 Drawing Sheets

PER VESSEL, VESSEL TREE MODELLING WITH SHARED CONTOURS

FIELD

Embodiments described herein relate generally to a method of, and apparatus for, modelling branching structures, for example in medical imaging applications. Embodiments have particular application in automatically determining contours of vessels of a vessel tree structure, particularly at or near branch points.

BACKGROUND

It is well known to use three-dimensional medical imaging techniques to obtain image data representative of structures within the body of a patient or other subject.

For example it is well known to use computerised tomography (CT) scanners to obtain three-dimensional image data representative of blood vessels or other structures. Usually, a contrast agent is injected into a blood vessel of the subject so that it passes through the blood vessels of interest. The presence of the contrast agent causes image data representative of the blood vessels obtained using the CT scanner to have a relatively high intensity and makes them easier to distinguish from surrounding tissue and other structures.

Blood vessels can also be imaged using a variety of other three dimensional imaging techniques, including for example MRI, PET or X-Ray Angiography.

A wide variety of techniques are known for the automatic processing of three dimensional image data in order to identify and model blood vessels and other branching structures. In many known techniques, the position of a centreline of the blood vessel or other branching structure is determined at a series of points along the structure, for example from analysis of the intensity profile of the structure. The points can then be joined or fitted to produce a centreline extending along the length of the blood vessel or other structure.

It can also be useful to determine contours, which represent the boundary of the blood vessels and other structures. For example, in the case of blood vessels, the contours can be used in subsequent procedures to automatically calculate the level of stenosis in a blood vessel from intensity levels and variations of image data representing points within the contours. Thus, rapid and accurate determination of contours can be important.

In some known techniques, contours for a series of points along a blood vessel are generated on planes which are largely perpendicular to the centreline of a blood vessel at those points. For each of the series of points along the blood vessel, a contour plane is determined, and the intensity profile of the data on that contour plane is analysed to determine the boundary of the blood vessel. The boundary at that point along the blood vessel is then represented by a contour.

However, although the centreline may be continuous, the curvature of the centreline is in general not smooth (the first derivative of the curve is not continuous). Although it is possible to smooth the centreline curve, for example by using a best fit algorithm, there is then a risk that the modified centreline would pass through calcium, or lie outside the vessel in some places. That point is illustrated with reference to FIGS. 1a, 1b and 1c.

Figures 1A, 1B:
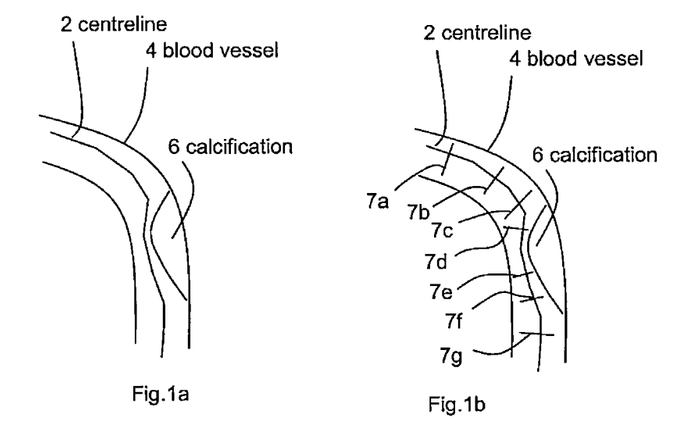
FIGS. 1a, 1b and 1c are schematic diagrams showing a blood vessel and centreline.

FIG. 1a shows a calculated centreline 2 of a blood vessel 4. It can be seen that the centreline is continuous but that it has sharp changes of direction along its length. The blood vessel includes a calcification or other obstruction 6. If the contour planes 7a, 7b, 7c, 7d, 7e, 7f, 7g (for example as illustrated in FIG. 1b) are taken as being perpendicular to the centreline at a series of points, it can be found that the resulting contours change direction too sharply. In some cases, contours determined just before and just after one of the changes of direction can overlap such that it can appear, incorrectly, that the blood vessel, represented by the contours, turns back on itself.

Figure 1C:
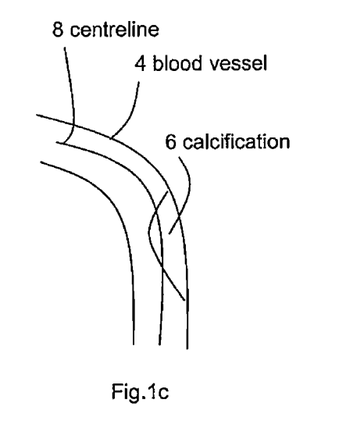

FIG. 1c shows the blood vessel 4 of FIG. 1a, but in this case the centreline has been smoothed. Whilst the smoothed centreline 8 may result in a smoothed series of contours, it can be seen that the smoothing has also resulted in the centreline 8 passing through the area of calcification rather than along the centre of the blood vessel 4.

It is possible for an operator to view images of the vessels or other structures overlaid with the calculated centrelines and contours, and to correct manually the position of the centreline or contours. However that can be time consuming and inefficient for the operator. Also, if the operator sees significant inaccuracies in the calculated centreline or contours, he or she may have reduced confidence in the image processing system that calculated the centreline or contours.

Figure 2:
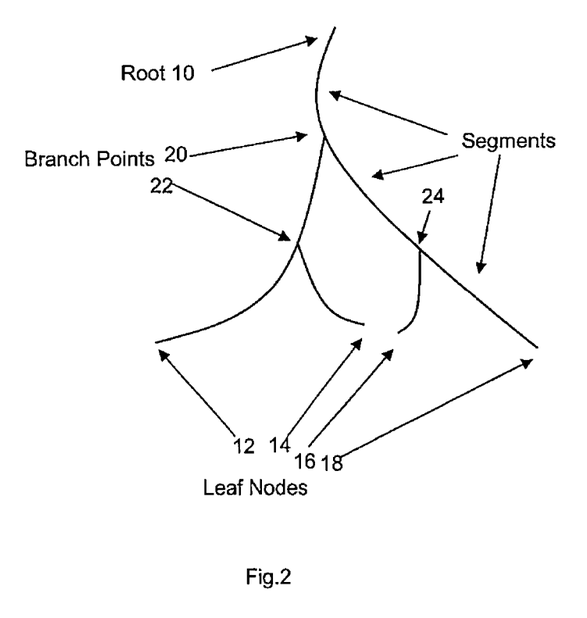
FIG. 2 is a schematic illustration of a branching structure.

Vessels in the body are often in the form of tree-like structures such as that illustrated schematically in FIG. 2. The vessel structure of FIG. 2 comprises a root node 10 that leads to various leaf nodes 12, 14, 16, 18 via branch points 20, 22, 24. A vessel may be considered to be a path from a root node 10 to a leaf node 12, which can pass through one or more branch points, or part of such a path. A segment may be considered to be a section of the structure from one branch point to the next branch point (for example, from branch point 20 to branch point 22) or from the root 10 to the next branch point 20.

In some known systems, contours can be calculated for different blood vessels separately, which means that contours may be recalculated several times for sections of the structure that form part of different blood vessels. For example, the segment between branch points 20 and 22 will form part of a blood vessel between the root node 10 and leaf node 12, and will also form part of a blood vessel between the root node and leaf node 14. It can be particularly time consuming for an operator if they have to manually adjust contours for segment or part of a segment for one blood vessel when they have already manually adjusted contours for the same segment or part of a segment when considering another blood vessel.

BRIEF DESCRIPTION OF THE DRAWINGS

Embodiments are now described, by way of non-limiting example, and are illustrated in the following figures, in which.

DETAILED DESCRIPTION

According to an embodiment there is provided a method of determining a contour of a model vessel representing a branching structure, wherein the structure comprising a branch point at which an upper segment of the structure splits into a first lower segment and a second lower segment, and the method comprises determining a path of a first model vessel representative of at least part of the upper segment and at least part of the first lower segment, determining a path of a second model vessel, representative of at least part of the upper segment and at least part of the second lower segment, determining the position of a contour branch point, and ensuring that for at least one position above the contour branch point a contour of the first model vessel is substantially the same as a contour of the second model vessel. The method may comprise ensuring that for ensure that for substantially all positions of the upper segment above the contour branch point, a contour of the first model vessel at a position is substantially the same as a contour of the second model vessel at that position.

Figure 3:
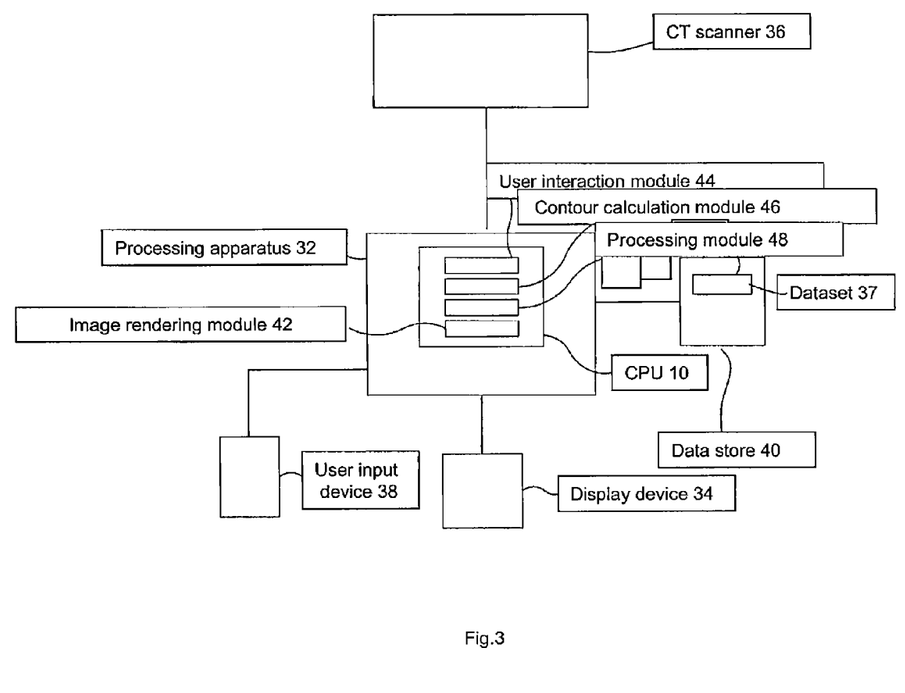
FIG. 3 is a schematic illustration of an apparatus according to an embodiments

An image processing apparatus according to an embodiment is illustrated schematically in FIG. 3 and is configured to implement the method described in the preceding paragraph. The apparatus comprises a processing apparatus 32, in this case a personal computer (PC) or workstation that is connected to a display device 34, a CT scanner 36 and a user input device or devices 38, in this case a computer keyboard and mouse. The processing apparatus is also connected to a data store 40.

Any suitable type of CT scanner may be used that is able to perform three dimensional CT measurements on a patient or other subject, for example one of the Aquilion® series of scanners produced by Toshiba Medical Systems Corporation. Although the embodiment of FIG. 1 is described in relation to CT scan data, any other suitable type of scanner producing any suitable type of image data may be used in alternative embodiments, for example MR data, of suitable form and if subject to suitable pre-processing, PET data or digital subtraction X-ray angiography data.

The processing apparatus 32 provides a processing resource for automatically or semi-automatically processing image data, and comprises a central processing unit (CPU) 10 that is operable to load and execute a variety of software modules or other software components that are configured to perform a method as described in detail below with reference to FIG. 4.

The processing apparatus includes an image rendering unit 42, a user interaction unit 44, a contour calculation unit 46, and an image data processing unit 48.

The image data processing unit is configured to determine a path of a first model vessel representative of at least part of an upper segment and at least part of a first lower segment, and for determining a path of a second model vessel, representative of at least part of the upper segment and at least part of a second lower segment, wherein the upper segment splits into a first lower segment and a second lower segment at a branch point.

The contour calculation unit 46 is configured to determine the position of a contour branch point and ensuring that for at least one position, or all positions, above the contour branch point a contour of the first model vessel is substantially the same as a contour of the second model vessel.

The processing apparatus 32 also includes a hard drive and other components of a PC including RAM, ROM, a data bus, an operating system including various device drivers, and hardware devices including a graphics card. Such components are not shown in FIG. 1 for clarity.

In the embodiment of FIG. 1, the processing apparatus 32 comprises a 2.0 GHz chipset and 2×4 core processors, that provide a multi-threaded environment using 9 threads, and 6.0 Gbytes of RAM is provided. However, any suitable CPU and other components may be used.

In the embodiment of FIG. 3, image data sets 37 are received by the processing apparatus 32 from the CT scanner 36 following performance of scans by the scanner 36, and are stored in the data store 40 and subsequently processed by the processing apparatus. Although the scanner 36 shown in the embodiment of FIG. 1 is a CT scanner, any other suitable type of scanner can be used to obtain the image data sets in alternative embodiments.

In a variant of the embodiment of FIG. 3, the processing apparatus 32 receives image datasets from a remote data store (not shown) rather than from the scanner 36. The remote data store stores a large number of different data sets obtained from many different scanners over a period of time together with associated patient data. The data store may be a server that stores a large quantity of patient data, and may form part of a Picture Archiving and Communication System (PACS), for example the Toshiba Rapideye® system.

Figure 4:
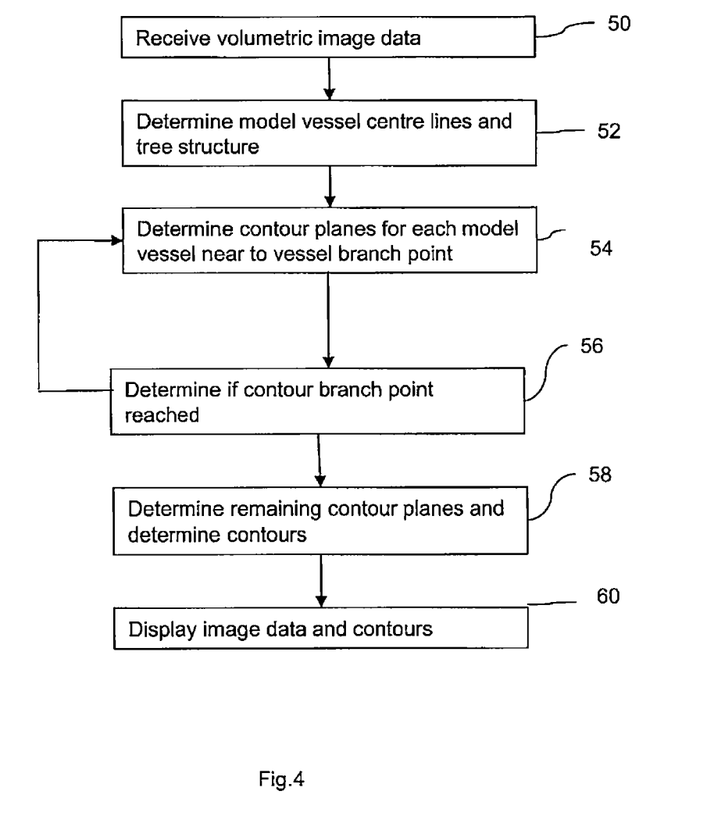
FIG. 4 is a flow chart illustrating in overview a process performed in accordance with an embodiment.

The system of FIG. 3 is configured to perform a process having a sequence of stages as illustrated in overview in the flow chart of FIG. 4.

At the first stage of the process, the image data processing unit 48 receives a volumetric image data set 37 from the data store 40. In this case, the dataset 37 comprises CT image data of a patient into whom contrast agent had been injected, and was obtained using the CT scanner 36.

The image data processing unit 48 performs known techniques for automatically identifying data representing blood vessel structures, for example coronary artery structures.

The image data processing unit 48 then, at stage 52, performs known techniques for generating centreline points along the centre of the blood vessels, and joining or fitting those points to obtain the centrelines. The centrelines form a treelike structure comprising vessels, segments, nodes and branch points, for example as illustrated schematically in FIG. 2.

At the next stage, the contour calculation unit 46 calculates contour planes for each of the model vessels of the structure. Each model vessel represents a path from one node to another node, for example from a root node to a leaf node, or represents part of such a path. Each model vessel can include several segments and branch points. The start and end points of each vessel may be selected manually by a user, for example to include points or regions of interest, or may be selected automatically. It will be understood that one model vessel may have one or more segments and branch points in common with another model vessel.

Figure 5:
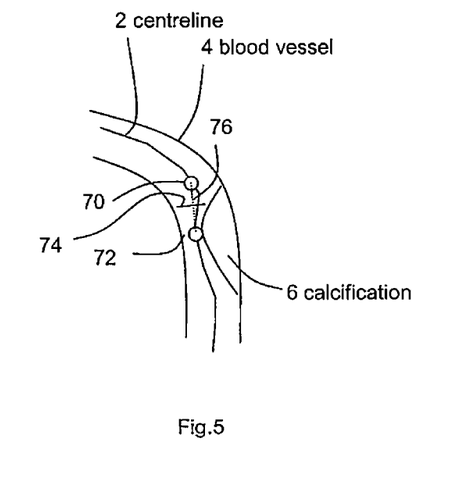
FIG. 5 is a further schematic illustration of a vessel.

It is a feature of the described embodiment that a contour plane at a particular position along the centreline of model vessel is determined in dependence on the position of centreline points both above and below that particular position, rather than being determined only in dependence on the centreline at that particular position. That feature is illustrated schematically in FIG. 5. FIG. 5 shows the blood vessel structure 4, the calculated centreline 2 and the calcification feature 6 that were illustrated in FIGS. 1a to 1c.

In the case of FIG. 5, the contour calculation unit 46 selects centreline points 70, 72 that are a predetermined distance along the centreline above and below the centreline point for which a contour is to be calculated. The contour calculation unit 46 then determines the contour plane 74 as being the plane perpendicular to a straight line 76 joining the contour points 70, 72 at the mid-point of the straight line 76. Thus, the contour plane at a particular point is determined from the direction of the centreline over a region of the vessel rather than the direction of the centreline at that particular point only. That can have the effect of smoothing variations in contour orientations, without affecting the position of the centreline.

Figure 6:
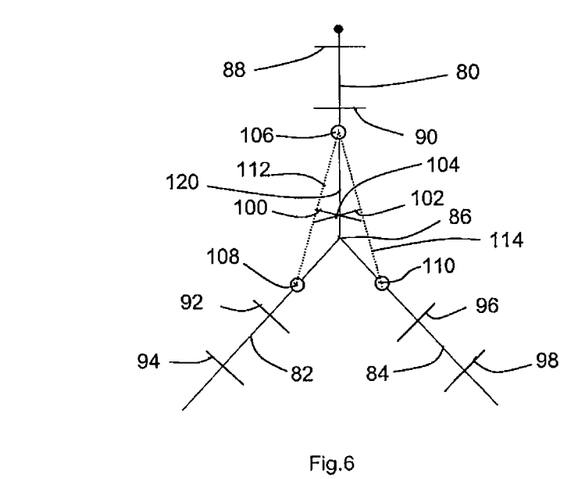
FIGS. 6 to 8 are schematic illustrations of a branching structure.

The contour calculation unit 46 can apply the process described in relation to FIG. 5 to determine contour planes for positions of structures at or near branch points, such as that illustrated in FIG. 6, which shows an upper segment 80 that divides at a branch point 86 into a first lower segment 82 and a second lower segment 84. A first model vessel is used to represent the upper segment 80 and the first lower segment 82. A second model vessel is used to represent the upper segment 80 and the second lower segment 84.

The contour calculation unit 46 begins by calculating contour planes for positions at or near the branch point 86 for both the first and second model vessels.

For example, with reference to FIG. 6, the contour plane 100 for the position 104 near the branch point is determined by the contour calculation unit 46 for both the first model vessel and the second model vessel. The contour plane for the first model vessel at position 104 is determined by selecting points 106 and 108 above and below position 104, joining the points 106 and 108 with a straight line 112 and determining the contour plane 100 to be the plane perpendicular to the straight line 112 at the midpoint of the straight line 112. Similarly, when calculating the contour plane 102 for the second model vessel at the same position 104, points 106 and 110 above and below that point 104 are selected, the points 106 and 110 are joined with a straight line 114 and the contour plane 102 is determined to be the plane perpendicular to the straight line 114 at the midpoint of the straight line 114.

However, as the lower points 108, 110 are below the branch point 86 they are different for the first model vessel and the second model vessel. Therefore, the contour planes 100, 102 are determined to be aligned in different directions for the first model vessel and for the second model vessel, as illustrated schematically in FIG. 6.

Figure 7:
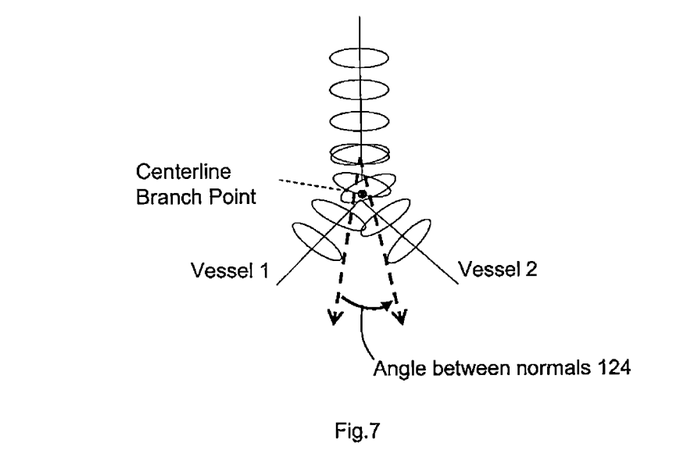

At the next stage 56 the contour calculation unit determines the direction normal to each of the contour planes 100, 102 and compares the angle 124 between the normals to those contour planes to a predetermined threshold value. In that case, the threshold is a threshold angle. The angle 124 between the normals is indicated in FIG. 7. If the angle 124 is greater than the predetermined threshold value then the contour planes 100, 102 at that position are treated as being different. The direction normal to the contour plane 100 can be considered to be a first contour parameter, and the direction normal to the contour plane can be considered to be a second contour parameter.

The contour plane determination procedure at stage 54 is then repeated for both the first model vessel and the second model vessel for the next point above the centreline branch point 86. The angle between the normals to the contour planes is again compared to the threshold and, if the angle is greater than the predetermined threshold the procedure is repeated for the next position above the centreline branch point 86.

Figure 8:
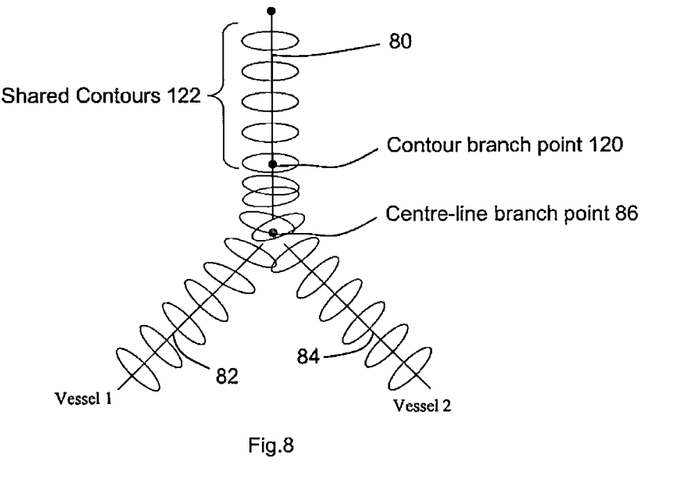

Progressing above the centreline branch point 86, the angles between the normals to the contour planes of the two vessels will gradually vanish to zero. If, at stage 56, the angle 124 between the normals to the contour planes is determined to be less than or equal to the predetermined threshold value, then that point is determined to be a contour branch point 120. Thus, the contour branch point is placed where the angle between the normals between the contour planes is considered acceptably close to zero. The contour branch point 120 is shown in FIG. 8, and it can be seen the contour branch point 120 is different to the vessel branch point 86.

Once the contour branch point has been determined, the procedure moves to stage 58, and contour planes are determined for all remaining positions. It is a feature of the described embodiment that for positions above the contour branch point 120 the contour planes are determined once, for one of the first model vessel and the second model vessel, and the contour planes for those positions are set to be the same for the other of the first model vessel and the second model vessel. Thus, some of the contour planes may be calculated once, rather than twice or more, which can save time and reduce processing burden.

In the example of FIG. 6, the contour planes 88, 90 for points on the upper segment a long way from the branch point 86 are the same for both the model vessels, and are calculated once and then used for both model vessels. The contour planes 92, 94, 96, 98, 100, 102 at and below the contour branch point are different for the different model vessels.

Contours are then determined for each of the positions from image data falling on the contour planes at those positions. Again, it is a feature of the described embodiment that for positions above the contour branch point 120 the contours are determined once, for one of the first model vessel and the second model vessel, and the contours for those positions are assigned to be the same for the other of the first model vessel and the second model vessel. Thus, some of the contours may be calculated once, rather than twice or more, which can again save time and reduce processing burden.

At the next stage 60, images representative of the structure together with the contours representing the boundaries of the structure may be rendered and displayed, under control of image rendering unit 42, on a graphical user interface (GUI) if desired. The contours may be connected in the image, to represent a continuous boundary of the structure.

The positions of the contours and the centrelines for one or both of the model vessels may be subject subsequently to manual editing by a user in certain embodiments. For example, in coronary analysis applications a user may view the image data representing a blood vessel and decide that the position of the centreline or contours for a model vessel should be moved to better represent the path or boundaries of the blood vessel. Depending on the details of the GUI, the user may alter the position of the centreline or contours by operation of mouse, for example using a drag and drop operation. The user interaction unit 44 receives the user input and makes the requested changes to the contours and/or centreline.

It is a feature of the embodiment described in relation to FIG. 4 that the contour calculation unit may be configured to, for positions above the contour branch point, automatically link a contour of the first model vessel at a position and a contour of the second model vessel at the same position, such that the contour for the second model vessel is changed automatically in response to a change in the first model vessel. Thus, if the user manually alters a contour for the first model vessel at a position above the contour branch point, then the same alteration is made automatically to the corresponding contour for the second model vessel. In contrast, for positions below the contour branch point, the user may alter contours for each of the first and second blood vessels independently of one another.

The embodiment described in relation to FIG. 4 can provide for the smoothing of variation in contours along a tree-like structure. The embodiment can also be useful in editing tree-like structures in an efficient manner. The original vessel centreline extracted by image analysis techniques does not need to be modified, and contours can appear connected smoothly, even at branch points. It can also be easy for users to edit shared contours, and it is possible for users to edit contours separately for each vessel near branch points. Performance can be enhanced by avoiding unnecessary duplication of contour generation.

Although in the described embodiment, the contour plane at a selected position along the centreline is determined as being normal to a straight line joining centreline points above and below that selected position, in alternative embodiments multiple centreline points above and below the selected position may be used to determine the contour plane. For example, two or more centreline points above the selected position and two or more centreline points below the selected position may be used, and may be fitted to a curve using any suitable curve-fitting technique. The contour plane in such embodiments is taken as being perpendicular to the fitted curve.

In the embodiment described in relation to FIGS. 6 to 8, the position of the contour branch point is determined by comparison to a predetermined threshold of the angle between the normals to the contour planes. In alternative embodiments, a different contour parameter is used to determine the similarity of the contours or the contour planes, and thus to determine the position of the contour branch point. For example, in one embodiment, the shapes of contours are compared and the average gap between the position of each contour at a series of positions along the centreline is determined. The contour branch point is then determined to position at which the average gap falls below a threshold value. Any other suitable contour parameter can be used in other embodiments.

In further alternative embodiments, the contour branch point is determined to be at a predetermined distance above the branch point. Thus, in such embodiments the position of the contour branch point may be determined without comparing contour parameters for the different model vessels.

Embodiments have been described with reference to an example in which a single segment splits at a branch point into two lower segments. However embodiments may also be used to model more complex tree structures, which include multiple branch points and/or multiple segments from each branch point.

Furthermore, whilst embodiments have been described in relation to CT measurements, the described embodiments may also be used to model image data obtained from any other imaging modality, including for example MRI, X-ray angiography, or PET imaging. Embodiments may be used to model any suitable structure that includes at least one branch point, and embodiments are not limited to modelling only blood vessel structures. For example, embodiments may be used to model vessels forming part of the lymphatic or nervous systems.

In another embodiment, there is provided a method of obtaining a smoothed vessel centreline comprising taking as input a vessel tree that comprises vessel centrelines composed of connected segments that can change direction discretely (rather than continuously and smoothly). At the vertex of connecting segment (the branch point), points may be located on the centreline on both sides of the vertex and away from vertex. The vector connecting such points may be taken as the normal for a contour at the vertex, and the collection of such contours may describe the vessel wall. Along with other contours, and their normals, they describe a smooth path for the vessel that is a useful and usable abstraction of the original data.

In another embodiment, there is provided a method of identifying vessel segments at a branch point using the vessel centreline by locating a point that lies on the smoothed centreline above said branch point, examining the normals for contours and the difference in the direction of these normals for each vessel segment below the located point and where this difference in direction becomes acceptably small identifying the separate segments as now being connected. Thus, vessels may be distinctly identified even at the branch point.

It will be well understood by persons of ordinary skill in the art that embodiments may implement certain functionality by means of a computer program having computer-readable instructions that are executable to perform the method. The computer program functionality could be implemented in hardware (for example by means of a CPU). However, the embodiments may also be implemented by one or more ASICs (application specific integrated circuit)) or by a mix of hardware and software.

Whilst particular units have been described herein, in alternative embodiments functionality of one or more of those units can be provided by a single unit, processing resource or other component, or functionality provided by a single unit can be provided by two or more units in combination. Units may be provided separately or in combination.

As used herein the terms upper and lower, and above and below, are intended only to indicate one side or another of a branch point. The terms upper and lower, and above and below, are not used to indicate relative height, or position in any particular co-ordinate system. For example, depending on the orientation of a patient or other subject, an upper segment or vessel may be positioned above, below or to the side of a lower segment or vessel, without limitation.

While certain embodiments have been described, these embodiments have been presented by way of example only, and are not intended to limit the scope of the inventions. Indeed the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms and modifications as would fall within the scope of the invention.

The invention claimed is:

1. An apparatus for determining a contour of a model vessel representing a branching structure, wherein the structure comprises a branch point at which an upper segment of the structure splits into a first lower segment and a second lower segment, the apparatus comprising:
   a processing circuit configured to
      determine a path of a first model vessel representative of at least part of the upper segment and at least part of the first lower segment,
      determine a path of a second model vessel, representative of at least part of the upper segment and at least part of the second lower segment, and
      determine a position of a contour branch point to ensure that for at least one position above the contour branch point, a contour of the first model vessel is substantially the same as a contour of the second model vessel,
   wherein the processing circuit is further configured to
      determine a first contour parameter for the first model vessel,
      determine a second contour parameter for the second model vessel,
      compare the first contour parameter and the second contour parameter,
      determine the position of the contour branch point in dependence on the comparison,
      for a series of positions away from the branch point, repeat the determining of the first contour parameter and the second contour parameter, and repeat the comparing of the first contour parameter and the second contour parameter, and
determine the position of the contour branch point to be substantially equal to a position at which the difference becomes less than or equal to a threshold.

2. The apparatus according to claim 1, wherein the processing circuit is further configured to ensure that for substantially all positions of the upper segment above the contour branch point, a contour of the first model vessel at a position is substantially the same as a contour of the second model vessel at that position.

3. The apparatus according to claim 1, wherein the processing circuit is further configured to determine, for the first model vessel, a first contour plane, and determine, for the second model vessel, a second contour plane.

4. The apparatus according to claim 3, wherein the processing circuit is further configured to determine the first contour parameter, which comprises a direction normal to the first contour plane, and the second contour parameter, which comprises a direction normal to the second contour plane.

5. The apparatus according to claim 1, wherein the processing circuitry is further configured to determine the first contour parameter, which comprises a direction normal to a first contour plane, and the second contour parameter, which comprises a direction normal to a second contour plane, and the threshold, which comprises a threshold angle between the normals to the first and second contour planes.

6. The apparatus according to claim 1, wherein the processing circuit is further configured to determine the position of the contour branch point to be a predetermined distance above the branch point.

7. The apparatus according to claim 1, wherein the processing circuit is further configured to, for positions above the contour branch point, calculate a contour plane for the first model vessel and set the contour plane for the second model vessel to be the same as the contour plane for the first model vessel.

8. The apparatus according to claim 1, wherein the processing circuit is further configured to, for a plurality of positions, calculate contours for the first model vessel and the second model vessel, and for positions above the contour branch point, the processing circuit is further configured to calculate a contour for the first model vessel at a position and set the contour for the second model vessel at that position to be the same as the contour for the first model vessel.

9. The apparatus according to claim 1, wherein the processing circuit is further configured to, for positions above the contour branch point, automatically link a contour of the first model vessel at a position and a contour of the second model vessel at the same position, such that the contour for the second model vessel is changed automatically in response to a change in the first model vessel.

10. The apparatus according to claim 9, further comprising a user interface for receiving user input, wherein the processing circuit is further configured to make the change to the first model vessel in response to the user input.

11. The apparatus according to claim 1, wherein the processing circuit is further configured to, for positions below the contour branch point, change a contour of the first model vessel at a position without changing a contour of the second model vessel at the same position.

12. The apparatus according to claim 3, wherein the processing circuit is further configured to:
select at least one first point on the path of the first model vessel above the branch point;
select at least one second point on the path of the first model vessel below the branch point;
calculate a line between the at least one first point above the branch point and the at least one second point below the branch point; and
determine, for a position of the first model vessel, the first contour plane to be a plane that is substantially perpendicular to the line.

13. The apparatus according to claim 12, wherein the processing circuit is further configured to determine the path of the first model vessel, which comprises a centerline, the at least one first point comprises at least one first centerline point, and the at least one second point comprises at least one second centerline point.

14. The apparatus according to claim 13, wherein the processing circuit is further configured to determine the path, which comprises the centerline, which comprises a succession of straight lines, each straight line joining successive centerline points.

15. The apparatus according to claim 12, wherein the processing circuit is further configured to calculate of the line between the at least one first point above the branch point and the at least one second point below the branch point, which comprises joining the points with a straight line, or fitting the line to the points.

16. The apparatus according to claim 1, wherein the processing circuit is further configured to determine contour planes for a series of positions along the first model vessel and to determine a respective contour at each contour plane, wherein the processing circuit is further configured to cause to be displayed to a user on a display an image of at least part of the branching structure and an image representing the contours.

17. The apparatus according to claim 1, wherein the processing circuit is further configured to determine the path representative of at least part of the upper segment of the structure, which splits at the branch point into the first lower segment, the second lower segment, and at least one further segment.

18. The apparatus according to claim 1, wherein the processing circuit is further configured to obtain three dimensional image data representative of the branching structure and to process the image data to determine the model vessel.

19. The apparatus according to claim 18, wherein the processing circuit is further configured to obtain the three dimensional image data, which comprises one of CT data, X-ray angiography data, MRI data, and PET data.

20. A method of determining a contour of a model vessel representing a branching structure, wherein the structure comprises a branch point at which an upper segment of the structure splits into a first lower segment and a second lower segment, the method comprising:
determining a path of a first model vessel representative of at least part of the upper segment and at least part of the first lower segment;
determining a path of a second model vessel, representative of at least part of the upper segment and at least part of the second lower segment;
determining the position of a contour branch point;
ensuring that for at least one position above the contour branch point a contour of the first model vessel is substantially the same as a contour of the second model vessel;
determining a first contour parameter for the first model vessel;
determining a second contour parameter for the second model vessel;
comparing the first contour parameter and the second contour parameter;

for a series of positions away from the branch point, repeating the determining of the first contour parameter and the second contour parameter, and repeating the comparing of the first contour parameter and the second contour parameter; and determining the position of the contour branch point to be substantially equal to a position at which a difference between the first contour parameter and the second contour parameter becomes less than or equal to a threshold.

21. A non-transitory computer-readable medium storing a computer program comprising computer-readable instructions that, when executed by a processor, cause the processor to perform the method according to claim 20.

* * * * *